(12) United States Patent
Lan et al.

(10) Patent No.: US 8,831,885 B2
(45) Date of Patent: Sep. 9, 2014

(54) INTEGRATED RADIOACTIVE SOURCE-FREE METHOD AND APPARATUS FOR POROSITY DETERMINATION: NMR CALIBRATED ACOUSTIC POROSITY

(75) Inventors: Chun Lan, Spring, TX (US); Songhua Chen, Katy, TX (US); Fabio Brambilla, Milan (IT)

(73) Assignee: Baker Hughes Incorporated, Houston, TX (US)

( * ) Notice: Subject to any disclaimer, the term of this patent is extended or adjusted under 35 U.S.C. 154(b) by 331 days.

(21) Appl. No.: 13/267,140

(22) Filed: Oct. 6, 2011

(65) Prior Publication Data

US 2012/0101732 A1 Apr. 26, 2012

Related U.S. Application Data

(60) Provisional application No. 61/406,300, filed on Oct. 25, 2010.

(51) Int. Cl.
| | | |
|---|---|---|
| G01V 3/38 | (2006.01) | |
| G01V 1/40 | (2006.01) | |
| G01V 3/18 | (2006.01) | |
| G01V 9/00 | (2006.01) | |
| G01N 24/08 | (2006.01) | |

(52) U.S. Cl.
CPC .................................. G01N 24/081 (2013.01)
USPC ........................................ 702/11; 73/152.06

(58) Field of Classification Search
CPC .......... G01V 3/32; G01V 11/00; G01V 3/38; G01V 5/04; G01V 2210/6167; G01N 24/081; G01N 2291/0231; G01N 29/07
USPC .................. 702/7, 8, 11, 12, 6; 324/303, 309, 324/323–377, 300; 73/152.01, 152.05, 73/152.14, 152.06; 175/50; 250/253
See application file for complete search history.

(56) References Cited

U.S. PATENT DOCUMENTS

| | | | | |
|---|---|---|---|---|
| 5,431,224 A | * | 7/1995 | Laali | 166/256 |
| 6,470,274 B1 | * | 10/2002 | Mollison et al. | 702/7 |
| 6,646,437 B1 | * | 11/2003 | Chitale et al. | 324/303 |
| 7,617,050 B2 | * | 11/2009 | Allen et al. | 702/7 |
| 7,710,823 B2 | * | 5/2010 | Tabarovsky et al. | 367/35 |
| 7,839,144 B2 | * | 11/2010 | Jebutu | 324/303 |
| 2009/0195246 A1 | | 8/2009 | Jebutu | |
| 2010/0256915 A1 | * | 10/2010 | Frost, Jr. | 702/9 |

OTHER PUBLICATIONS

McKenzie, J.A. Davies, P.J., Palmer-Julson, A. et al 1993 (Resistivity/Porosity/Velocity Relationships from Downhole Logs: An Aid for Evaluating Pore Morphology) teaches well-known relationships between formation parameters.*
Wyllie, M.R. et al., "Elastic wave velocities in heterogeneous and porous media," Geophysics, vol. 21, No. 1, pp. 41-70 (1956).
Raymer, L.L., et al., "An improved sonic transit time to porosity transform," SPWLA 21st Annual Logging Symposium (1980).
Minh C.C., et al., "Sonic-magnetic resonance method: A sourceless porosity evaluation in gas-bearing reservoirs," SPE72180 (2001).

* cited by examiner

*Primary Examiner* — Sujoy Kundu
*Assistant Examiner* — Lisa Peters
(74) *Attorney, Agent, or Firm* — Mossman Kumar & Tyler PC

(57) ABSTRACT

NMR porosity measurements made in a gas free-formation are used to calibrate acoustic measurements. The calibration parameters are then used in conjunction with estimates of shale content to provide improved estimates of formation porosity in shaly intervals which may include a gas.

18 Claims, 4 Drawing Sheets

INTEGRATED RADIOACTIVE SOURCE-FREE METHOD AND APPARATUS FOR POROSITY DETERMINATION: NMR CALIBRATED ACOUSTIC POROSITY

CROSS-REFERENCES TO RELATED APPLICATIONS

This application claims priority from U.S. Provisional Patent Application Ser. No. 61/406,300, filed on Oct. 25, 2010, incorporated herein by reference in its entirety.

FIELD OF THE DISCLOSURE

This disclosure relates to apparatus and techniques for making porosity measurements of an earth formation without using radioactive sources. Specifically, the disclosure relates to the design of an accurate acoustic measurement technique which, when calibrated with NMR measurements, gives the porosity of an earth formation over a wide range of lithologies and in the presence of gas in the formation.

BACKGROUND OF THE DISCLOSURE

Oil well logging has been known for many years and provides an oil and gas well driller with information about the particular earth formation being drilled. In conventional oil well logging, after a well has been drilled, a probe known as a sonde is lowered into the borehole and used to determine some characteristic of the formations which the well has traversed. The probe is typically a hermetically sealed steel cylinder which hangs at the end of a long cable which gives mechanical support to the sonde and provides power to the instrumentation inside the sonde. The cable also provides communication channels for sending information up to the surface. It thus becomes possible to measure some parameter of the earth's formations as a function of depth, that is, while the sonde is being pulled uphole. Such "wireline" measurements are normally done in real time (however, these measurements are taken long after the actual drilling has taken place).

Porosity measurements are commonly done by using a dual detector neutron logging tool using a source of neutrons irradiating the formation being studied. Density measurements are commonly done by using a dual detector gamma ray logging tool using a source of gamma rays irradiating the formation being studied. The density measurements, and some of the porosity measurements, may require the use of a radioactive source of neutrons and/or gamma rays. From a safety standpoint, the use of radioactive sources is problematic, particularly for measurement while drilling (MWD) applications.

Radioactive-source-free tools, such as Nuclear Magnetic Resonance (NMR) and acoustic logging have been used in the past for porosity determination. NMR logging has the advantage of directly measuring fluids in pore space and, thus, does not suffer from the lithology effect on porosity determination. However, the accuracy of NMR total porosity in gas-bearing formations is affected by low hydrogen index (HI) and the ability to separate gas and liquid NMR responses. In the cases of extremely viscous oil-bearing reservoirs, coal-bed methane-bearing formation or gas-hydrates, the hydrocarbon signals may relax too fast to be observed by the state of art NMR well logging instruments, thereby causing under-estimation of porosity. On the other hand, acoustic measurements respond to lithology and texture in addition to porosity. Consequently acoustic porosity is an indirect measurement based on empirical or semi-empirical models, which often requires calibration of model parameters.

Integrating acoustic and NMR measurements for gas-zone porosity estimation has been reported in relatively clean sandstones. However, the existing methods in literature have not been extended to shaly sandstones. The present disclosure describes a radioactive source-free porosity estimation method using NMR logs to calibrate acoustic porosity models. This approach is applicable to clean and shaly sandstones using wireline and logging while drilling (LWD) measurements.

SUMMARY OF THE DISCLOSURE

In view of the foregoing, the present disclosure is directed to a method and apparatus for making porosity measurements of an earth formation without using a radioactive source. In particular, the present disclosure is directed to acoustic measurements calibrated with NMR measurements and used to estimate porosity of an earth formation over a range of lithologies and in the presence of gas in the formation.

One embodiment of the disclosure includes a method of estimating a value of a porosity of an earth formation comprising a first solid component, a second solid component, and a gas. The method includes: using an acoustic tool for making a measurement indicative of a porosity of the earth formation in an interval that includes (i) a gas, (ii) the first solid component, and (iii) the second solid component; and using a processor for: estimating the value of the porosity in the interval using the measurement made by the acoustic tool, a fractional value of the second component, and at least one parameter relating an additional measurement made by the acoustic tool to a measurement by a nuclear magnetic resonance (NMR) tool in another interval that does not include a gas.

Another embodiment of the disclosure includes an apparatus configured to estimate a value of a porosity of an earth formation comprising a first solid component, a second solid component and a gas. The apparatus includes: an acoustic tool configured to make a measurement indicative of a porosity of the earth formation in an interval that includes: (i) a gas, (ii) the first solid component, and (iii) the second solid component; and a processor configured to: estimate a value of the porosity in the interval using the measurement made by the acoustic tool, a fractional value of the second component and at least one parameter relating an additional measurement made by the acoustic tool to a measurement by a nuclear magnetic resonance (NMR) tool in another interval that does not include a gas.

Another embodiment of the disclosure is a tangible computer-readable medium product having stored thereon instructions what when read by a processor cause the processor to execute a method. The method includes: estimating a value of a porosity of a formation, using a measurement made by an acoustic tool in a borehole in an interval containing a first solid component, a second solid component, and a gas; a fractional value of the second component; and at least one parameter relating an additional measurement made by the acoustic tool to a measurement by a nuclear magnetic resonance (NMR) tool in another interval that does not include a gas.

BRIEF DESCRIPTION OF THE DRAWINGS

The present disclosure is best understood with reference to the following figures in which like numerals refer to like elements, and in which.

DETAILED DESCRIPTION OF THE DISCLOSURE

Figure 1:
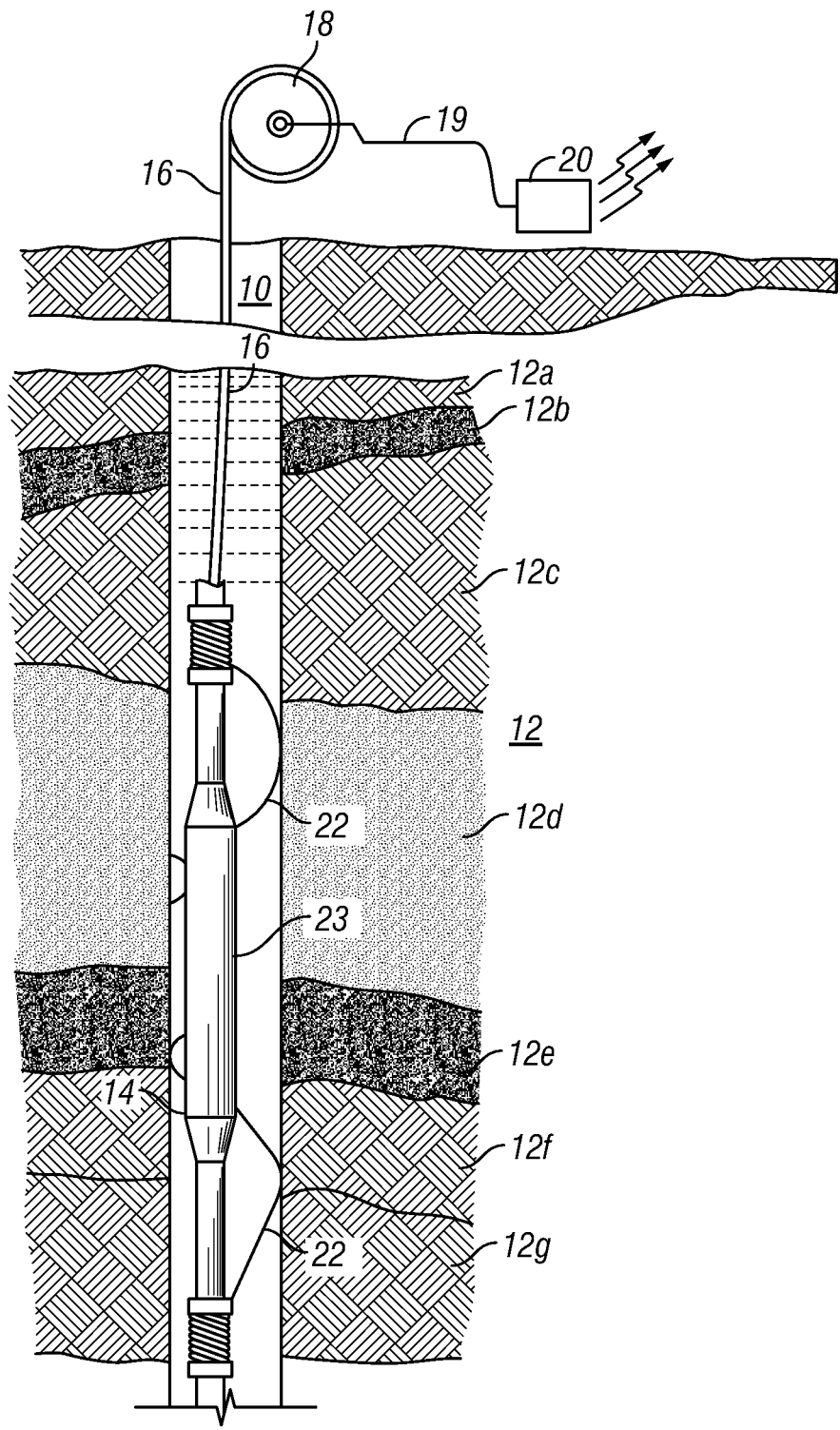
FIG. 1 depicts diagrammatically an NMR logging tool in a borehole according to one embodiment of the present disclosure.

FIG. 1 depicts a borehole 10 drilled in a typical fashion into a subsurface geological formation 12 to be investigated for potential hydrocarbon producing reservoirs. An NMR logging tool 14 has been lowered into the borehole 10 using a cable 16 and appropriate surface equipment (represented diagrammatically by a reel 18) and is being raised through the formation 12 comprising a plurality of layers 12a through 12g of differing composition, to log one or more of the formation's characteristics. The NMR logging tool may be provided with bowsprings 22 to maintain the tool in an eccentric position within the borehole with one side of the tool in proximity to the borehole wall. The permanent magnets 23 provide the static magnetic field. Signals generated by the tool 14 are passed to the surface through the cable 16 and from the cable 16 through another line 19 to appropriate surface equipment 20 for processing, recording, display and/or for transmission to another site for processing, recording and/or display. Alternatively, the processor may be located at a suitable position (not shown) downhole, e.g., in the logging tool 14. It should be noted that the use of a wireline-conveyed NMR tool is for illustrative purposes only and the method of the present disclosure can be implemented using a logging tool conveyed on a bottomhole assembly by a drilling tubular.

In the method of the present disclosure, two models are used. One is a model relating acoustic measurements to formation porosity and the other is a model relating NMR measurements to an estimated formation porosity. The NMR model is discussed first.

The total porosity $\phi_{t,NMR}$ made by an exemplary NMR logging tool is given by the relation:

$$\phi_{t,NMR} = \phi S_w I_{Hw}\left(1 - e^{\frac{t_w}{T_{1w}}}\right) + \phi(1 - S_w)I_{Hg}\left(1 - e^{\frac{t_w}{T_{1g}}}\right), \quad (1)$$

where $\phi$ is the formation porosity, $S_w$ is the water saturation, $I_{Hw}$ and $I_{Hg}$ are the hydrogen indices of water and gas respectively, $T_{1w}$ and $T_{1g}$ are the longitudinal relaxation times of water and gas respectively, and $t_w$ is the wait time of the NMR pulsing. In gas-bearing formations logged with insufficient wait time, the low HI of the gas cause $\phi_{t,NMR}$ to be less than the true total porosity of the formation. The NMR measurement made in a gas-free formation may be referred to as a "first measurement" made in a first interval.

The present disclosure is illustrated using the Raymer-Hunt-Gardner (RHG) time transform, which is primarily developed for clean formations. The RHG transform for compressional wave can be written as:

$$\phi_{acoustic} = \frac{\Delta t_p - \Delta t_{p,ma}}{\Delta t_p}C, \quad (2)$$

where $\Delta t_p$ is the measured compressional wave slowness, $\Delta t_{p,ma}$ is the compressional wave slowness of the dry matrix, and C is a fitting parameter. We note that C has low sensitivity to fluid typing, and is fairly stable and often can be treated as a constant. However, as the porosity increases, eqn. (2) becomes more sensitive to fluid typing.

The RHG equation for shear waves can be written as:

$$\frac{1}{\Delta t_s} = \frac{(1 - \phi)^2}{\Delta t_{s,ma}}, \quad (3)$$

where $\phi$ is the total porosity of the formation, $\Delta t_s$ is the measured S-wave slowness in the formation, and $\Delta t_{s,ma}$ is the S-wave slowness of the dry matrix. This equation assumes the S-wave modulus does not depend on the pore fluid.

With respect to the RHG method, if the formation is pure sandstone, limestone, or dolostone, $\Delta t_{ma}$ is a constant number, which can be found in literature. Thus, the formation includes a first component (the matrix) that may be made of quartz, calcium carbonate or magnesium/calcium carbonate.

If the formation of interest includes shale, $\Delta t_{ma}$ can vary with the shale type, distribution, and percentage. This makes $\Delta t_{ma}$ highly unpredictable for complex-lithology reservoirs. In the method described in this disclosure, a basic assumption that is made is that within a certain depth interval, there is a good consistency of $\Delta t_{ma}$ on the shale type and distribution. $\Delta t_{ma}$ then only varies with fractional shale percentage and the fitting parameter C in the RHG transform is considered to be constant.

Under such assumptions, NMR logs are used for calibration in the liquid-bearing zones to serve two main purposes.

1. Calibrate the fitting parameter in the RHG transform.

2. Extract the correlation between $\Delta t_{ma}$ and the fraction of shale content.

The Fractional Shale Volume (FSV) can be estimated by one or more of the downhole measurement techniques, e.g., a Gamma Ray (GR) log, a spectral GR log, a Potassium-Thorium (KTh) log, a clay bound water (CBW) log, or an acoustic log that measures compressional wave velocity ($V_p$) and shear wave velocity ($V_s$), or a ratio between these velocities ($V_p/V_s$). The CBW log is obtained using an NMR tool in the shaly interval.

With respect to GR: the Natural GR log, which is mainly responsive to potassium, uranium, and thorium, has been widely used as shale indicator. The potassium spectrum log of the GR response is indicative of clay minerals. For heavy oil or Kerogen-rich shales, the uranium may exist in the hydrocarbon or biomass rather than in shale matrix. Hence spectral GR logs, which separately determine K, Th, and U, may be used as shale indicators and for quantifying shale volume. Although, in general, the correlation between GR response and fractional shale content is complex and can be affected by many factors, a commonly-used simplified linear correlation model is an adequate approximation to interpret fractional shale volume (FSV) for many underground rock formations:

$$V_{shale} = \frac{GR - GR_{min}}{GR_{max} - GR_{min}}, \quad (7)$$

where GR is the Gamma Ray reading at each depth, $GR_{min}$ is the minimal GR reading in the interval, often corresponding to the clay-free sand (i.e., clean sand) and $GR_{max}$ is the GR reading from shale. Note, the total GR in eqn. (7) can be the total GR, or one or more of the spectral GR components.

With respect to CBW: Volume of clay bound water (CBW) represents the porosity in clay or shale content in a formation rock. From NMR logs, both the fractional porosity from CBW ($\phi_{CBW}$) and the total porosity ($\phi_{T,NMR}$) may be obtained.

$$\frac{\phi_{CBW}}{\phi_{T,NMR}}$$

may be used to identify the fraction of shale content in a rock formation. If there is no shale content, then $$\frac{\phi_{CBW}}{\phi_{T,NMR}} = 0,$$

and, if it is in a pure shale zone, then $$\frac{\phi_{CBW}}{\phi_{T,NMR}} = 1.$$

$\phi_{CBW}$ is usually determined by integration of the NMR signal corresponding to the relaxation time smaller than or equal to a pre-determined clay-bound water cutoff value: $T_2 \leq T_{2\ cutoff\ (CBW)}$. However, the use of such criterion in carbonate formation should be with great caution, as the microporosity has the similar NMR relaxation time signature as that of clay bound water.

With respect to $V_p/V_s$ ratio: $V_p/V_s$ varies with lithology of the formation and has been used as indicator of lithology based on "Pickett's crossplot". Based on the current literature, $V_p/V_s$ ratio of 1.9 is often used for limestones, 1.8 for dolostones, and in the range of 1.6 to 1.8 for clean sandstones. The shale content is also known to increase the $V_p/V_s$ ratio compared to the value in the clean formation. Based on the Biot-Gassmann theory, the $V_p/V_s$ ratio can be affected by porosity, fluid typing, lithology, etc. When the porosity is below 25 pµ, the pore space modulus, $K_p$, become relatively very small, and then can be neglected, which makes the $V_p/V_s$ ratio become porosity and fluid independent. Therefore, $V_p/V_s$ can be considered as a good shale content indicator when the porosity is below 25 pµ. It can be used in both sandstones and carbonates. More details on the related acoustic theory are attached in Appendix A.

The primary acoustic porosity model used in this method is the RHG transform; the current disclosure comprises procedures using P-wave data and S-wave data.

P-Wave Interpretation

P-wave interpretation is the primary approach (compared to S-wave approach) and may be used for the formation with porosity less than 25 pµ. It contains a method and procedure for determining the constant fitting parameter C and the matrix slowness. The matrix slowness varies with the shale content associated with any particular earth depth. The procedure can be summarized in the following three steps:

A. Calibrate the Fitting Parameter C:

A clean (i.e., shale-free) liquid-bearing sands logging interval is used in this step. The term "clean liquid bearing interval" refers to a liquid bearing zone with little shale content. In the clean liquid-bearing interval, NMR total porosity $\phi_{T,NMR}$ is not affected by the uncertainty of saturation determination or HI, thus its porosity value is used as the true porosity associated with the corresponding depth, and, thus, is used to calibrate the acoustic porosity equation constant, which can be written as:

$$S_{liquid}=1 \Rightarrow \phi_{acoustic}=\phi_{T,NMR}.$$

As noted above, the clean liquid bearing interval comprises a matrix of quartz, calcium carbonate or magnesium/calcium carbonate.

It is noted that the HI of some liquid phase fluids in the formation, such as high-salinity water, may be slightly smaller than 1. Correction of HI for those fluids is generally known to be trivial and not expected to introduce significant error even if the fluid saturation is not highly accurate. Both $\Delta t_{p,ma,clean}$ (since it is in the clean matrix, $\Delta t_{p,ma,clean}=\Delta t_{p,ma}$) and C in the RHG are constant values, which are obtained simultaneously by fitting the RHG transform eqn. (2).

In this disclosure, the fitting parameter C is assigned to be the same for clean and shaly sands, base on the assumption that clay content does not drastically change the grain structure. Clean sands comprise primarily quartz. The assumption of a grain supported structure is valid if the clay is authigenic clay, which is only located in the pores or on the surface of grains. Such authigenic clay has little impact on the acoustic property in the grain supported structure. Authigenic clay is usually restricted to less than 40% of total volume. The clay forms the second component of the formation.

B. Calibrate the $\Delta t_{p,ma}$ at Each Depth in the Zone of Interest

The second step is to calculate $\Delta t_{p,ma}$ for each depth in the zone of interest (gas bearing zone) by extracting the correlation between $\Delta t_{p,ma}$ and the shale fraction. The estimation of FSV may be done using GR, CBW, or $V_p/V_s$ ratio, or any combination of these, depending on the particular formation lithology, general porosity range, and data quality. The criteria for choosing the right candidate is described in the previous section: "The Fractional Shale Volume". Here we named the values of the selected candidate as "x". For instance, if we choose CBW, then "x" is $$\frac{\phi_{CBW}}{\phi_{T,NMR}}.$$

If GR is used, then "x" may be estimated from eqn. (7) or from a K log. If $V_p/V_s$ is used, then "x" is the $V_p/V_s$ ratio.

In order to calibrate $\Delta t_{p,ma}$ for a shaly sand formation, liquid-bearing zones with some shale contents are required. This can be either a shaly interval ($V_{shale}<1$) or full-shale interval ($V_{shale} \to 1$). There are two alternative approaches to calibrate $\Delta t_{p,ma}$ depending on whether $V_{shale}<1$ or $V_{shale} \to 1$ is used for calibration.

In one embodiment of the disclosure, the correlation between $\Delta t_{p,ma}$ and "x" in the clean and shaly zone is mapped. The matrix slowness in these zones can be back-calculated from Raymer-Hunt-Gardner by using C calibrated from the clean liquid-bearing zone:

$$\Delta t_{p,ma,clean} = \Delta t_p - \frac{\phi_{T,NMR}}{C}\Delta t_p. \quad (8)$$

Polynomial functions can be used to provide a good fitting to the data trend, which may sometimes be a simple first order linear function. Finally $\Delta t_{p,ma}$ in the gas zone can be calculated by applying "x" at each depth into the fitting function. It should be noted that the notation herein makes a distinction between $\Delta t_{p,ma,clean}$ for a clean dry matrix and $\Delta t_{p,ma,shale}$ for a shale formation.

Figure 2:
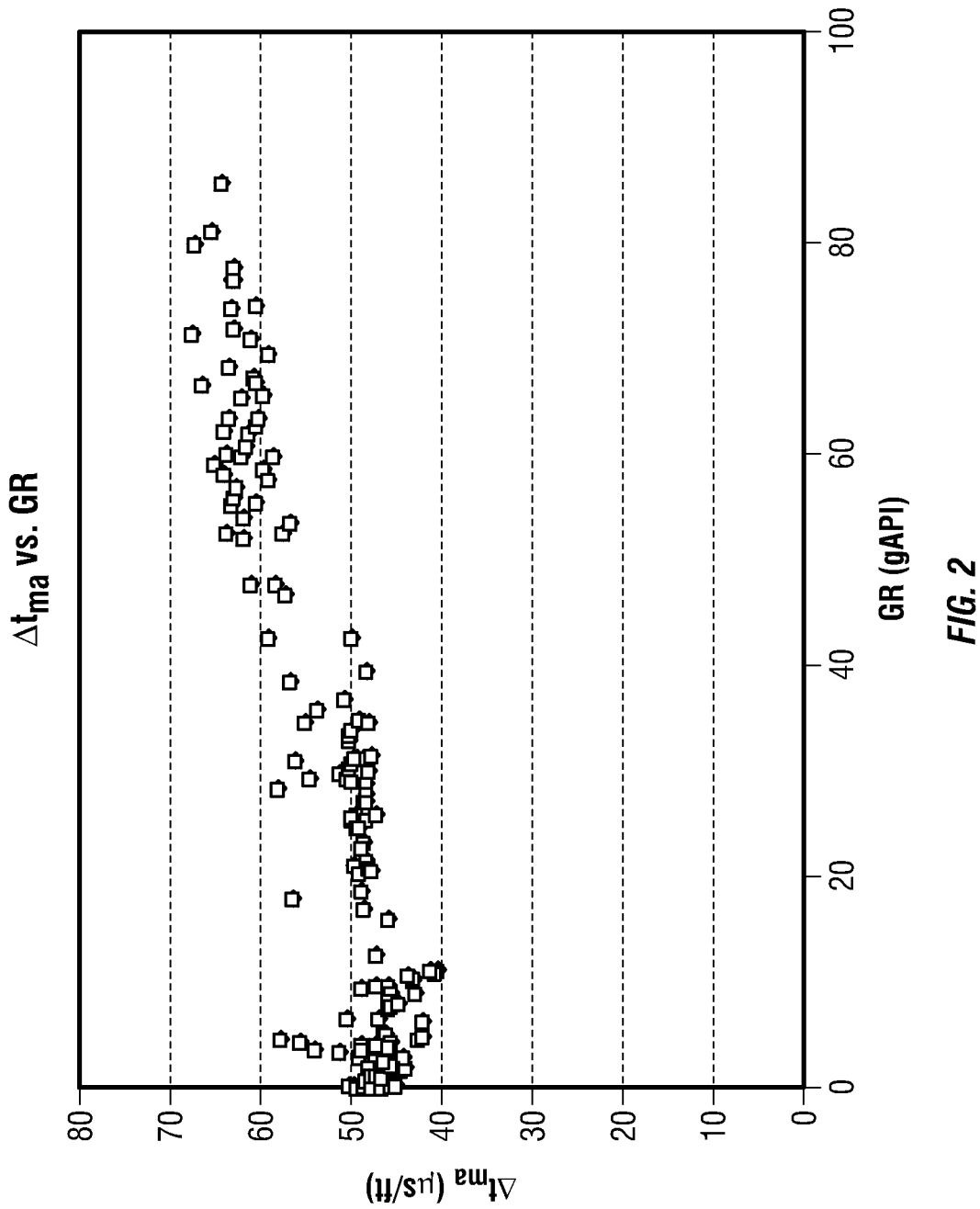
FIG. 2 shows plot of $\Delta t_{ma}$ vs. GR in the water bearing zones.

An example of using GR as shale indicator can be used to demonstrate the calibration process. FIG. 2 shows the plot of $\Delta t_{ma}$ vs. GR in the water bearing zones, where $\Delta t_{ma}$ is calculated using the fitting parameter C pre-calibrated in clean water-bearing zone in the first step of the calibration. In this case, we used linear correlation:

$$\Delta t_{ma} = a \cdot GR + b \quad (9).$$

Alternatively, a formation-specific correlation can be used if sufficient historical log or core data in the substantial similar earth formation exist. In the gas zone, assuming $\Delta t_{ma}$ and GR has the same correlation as shown in eqn. (9), $\Delta t_{ma}$ in the gas-bearing zone can then calculated for each depth. An example is illustrated in FIG. 2.

Calibrate $\Delta t_{p,ma}$ from a nearby shale zone. In Wyllie time average equation, measured compressional wave slowness may be expressed as:

$$\Delta t_p = \Delta t_{p,ma,shale}(1 - \phi_{T,NMR}) + \Delta t_{fl}\phi_{T,NMR} \quad (10)$$

where $\Delta t_{p,ma,shale}$ and $\Delta t_{fl}$ are the shale and fluid slowness to calibrate the shale slowness $\Delta t_{p,ma,shale}$ The slowness of the rock matrix is a weighted average between the slowness of the clean matrix and the slowness of the shale, as shown in eqn. (11)

$$\Delta t_{p,ma} = \Delta t_{p,ma,clean}(1 - V_{shale}) + \Delta t_{p,ma,shale}V_{shale}, \quad (11)$$

where $V_{shale}$ is the FSV, which can be calculated from "x" corresponding the depth of the gas-bearing zone. A linear correlation between $V_{shale}$ and "x" is used in the current method, although other correlation can be used as well. For instance, if GR is used for "x", eqn. (7) is used to calculate $V_{shale}$.

C. Calculate the NMR Calibrated Acoustic Porosity in the Zone of Interest

After the calibration process, parameters C and $\Delta t_{p,ma}$ in the gas-bearing zone are known. Applying them into the RHG transform, eqn. (2), the porosity in the gas-bearing zone can be determined.

S-Wave Interpretation

This approach may be used for formation with porosity higher than 25 pu or when P-wave interpretation is not available. In a manner similar to the P-wave-based porosity interpretation, the S-wave-based interpretation also requires a calculation of the dry matrix slowness curve in the gas-bearing interval and further calculation of the porosity. As the RHG equation for S-wave contains only one parameter $\Delta t_{s,ma}$, the first step in the P-wave interpretation for calibrating C is skipped. The S-wave interpretation procedure is similar to the procedure in P-wave interpretation, which is outlined below.

1. Calculate $\Delta t_{s,ma}$ at Each Depth in the Zone of Interest

One or a few nearby water-bearing intervals are selected for calibration. In the calibration interval(s), $\Delta t_{s,ma}$ can be calculated from eqn. (12):

$$\Delta t_{s,ma} = (1 - \phi_{T,NMR})^2 \cdot \Delta t_s, \quad (12)$$

where NMR total porosity is used as the reference porosity in the water-bearing interval. A correlation between $\Delta t_{s,ma}$ and curve "x" can then be established and by applying the same correlation into the gas-bearing interval, $\Delta t_{s,ma}$ in the gas-bearing interval can be calculated. Calibration intervals may be selected for S-wave interpretation without clean-sand intervals. Unlike in P-wave interpretation, the parameter C may not be performed in S-wave interpretation.

2. Calculate the NMR-Calibrated Acoustic Porosity in the Zone of Interest

After $\Delta t_{s,ma}$ in the gas-bearing interval is calculated, by applying $\Delta t_{s,ma}$ to the RHG transform, eqn. (12), the porosity in the gas-bearing interval can be determined. Finally the process of calculating NMR calibrated acoustic porosity can be summarized in the following flow charts.

Figure 3:
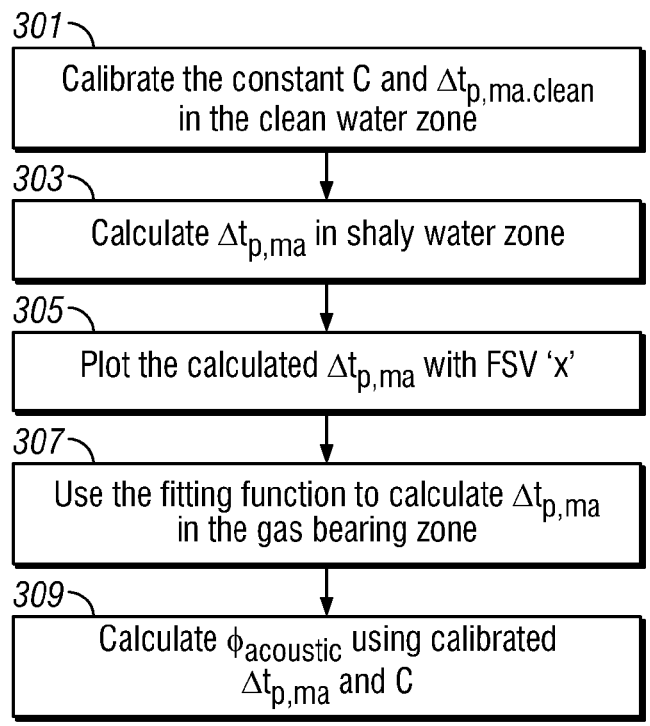
FIG. 3 shows a flow chart of one embodiment of a method according to the present disclosure.

In the embodiment disclosed in the flow chart of FIG. 3, the constant C and the slowness $\Delta t_{p,ma}$ in the clean water zone are determined 301. The $\Delta t_{p,ma}$ in the shaly water zone may be determined 303. In the embodiment of FIG. 3, this is done by establishing the correlation between $\Delta t_{p,ma}$ and "x" 305 using the FSV. The fitting function found in 305 may be used to calculate $\Delta t_{p,ma}$ in the gas bearing zone 307. The acoustic porosity may be calculated using the calibrated C and $\Delta t_{p,ma}$ 309.

Figure 4:
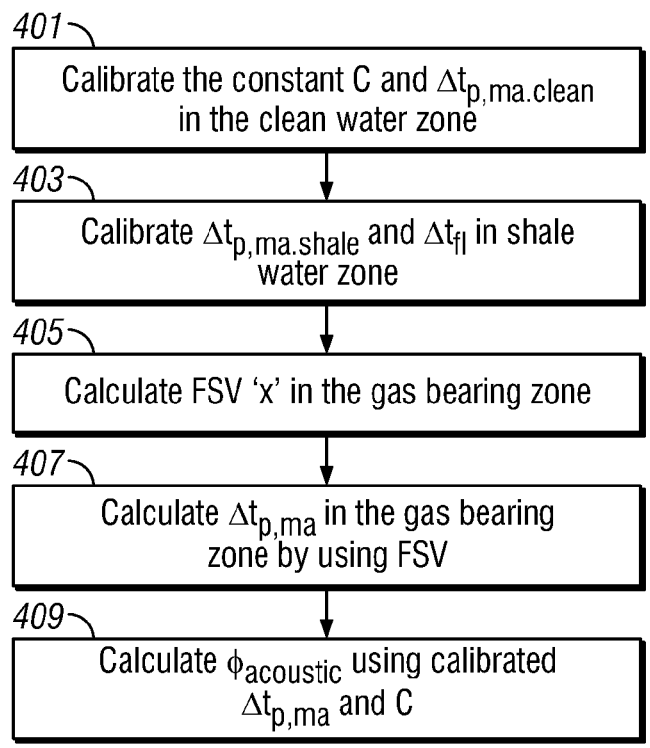
FIG. 4 shows a flow chart of another embodiment of a method according to the present disclosure.

The embodiment disclosed in FIG. 4 has many steps in common with the flow chart of FIG. 3. Step 401 may be the same as steps 301. Using, for example, the Wylie time average equation, $\Delta t_{p,ma,shale}$ is obtained from $\Delta t_{p,ma,shale}$ and $\Delta t_{fl}$ 403. The FSV "x" may be calculated for the gas bearing zone 405. Using eqn. (11), $\Delta t_{p,ma}$ may be calculated 407, and the acoustic porosity may be calculated 409. In this embodiment, step 403 is implemented using $\Delta t_{p,ma,shale}$ from a nearby shale zone. The estimated FSV may be sensitive to the value of $GR_{min}$ and $GR_{max}$ in eqn. (7). Consequently, in one embodiment, the average value of $GR_{min}$ in a clean formation is used and the average value of $GR_{max}$ in a shale zone is used.

Figure 5:
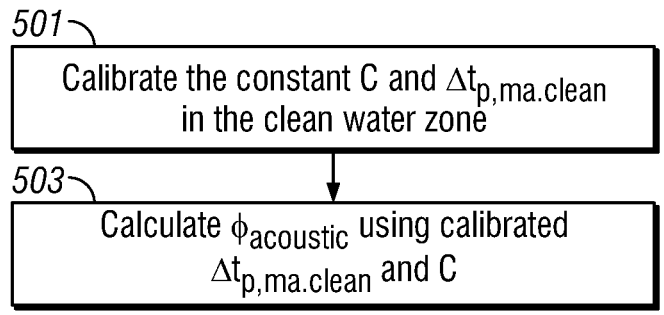
FIG. 5 shows a simplified flow chart of a method for a clean formation according to one embodiment of the present disclosure.

FIG. 5 shows an embodiment of the disclosure for use with clean formations. Step 501 is the same as steps 301 and 401 while step 503 is the same as steps 309 and 409

Figure 6:
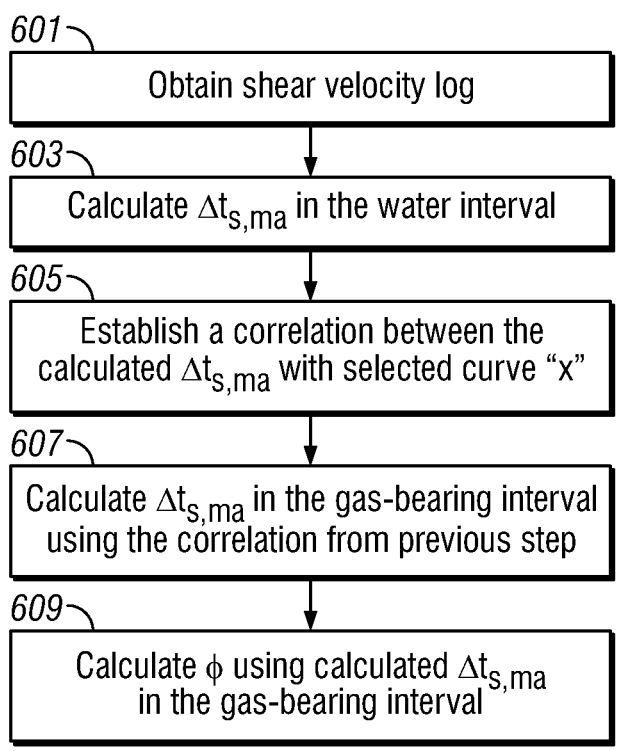
FIG. 6 shows a simplified flow chart of a method for using shear waves according to one embodiment of the present disclosure.

FIG. 6 shows a flowchart of an embodiment of the disclosure using shear velocity measurements. A shear velocity log is obtained 601. This may be done using any of suitable prior art devices for the purpose, for example, the device disclosed in U.S. Pat. No. 4,606,014 to Winbow. The value of $\Delta t_{s,ma}$ in the water interval is calculated 603. A correlation is established between $\Delta t_{s,ma}$ and the selected curve. The value of $\Delta t_{s,ma}$ in the gas-bearing interval is estimated 607 using the established correlation from 605. The estimated value of $\Delta t_{s,ma}$ in the gas-bearing interval may be used to calculate the porosity $\phi$609.

With respect to FIGS. 3, 4, and 6, illustrating three methods, a measurement is made by an acoustic tool that is indicative of the porosity of the formation. This measurement is made in an interval that includes a first solid component and also contains a second solid component and/or a gas. The porosity is then estimated using the acoustic measurement, a fractional value of shale (the second solid component) and the results of calibration of a measurement made by the acoustic tool in another interval that does not include gas. Depending on whether the acoustic measurement is of a compressional wave or a shear wave, the calibration may be characterized by one or two parameters.

In one embodiment of the disclosure, the results of the calibration may be stored in a table and a table look-up may be used to estimate the formation porosity using the acoustic measurement and the fractional shale volume.

The method of the present disclosure is described above with reference to a wireline-conveyed NMR logging tool. The method may also be used on logging tools conveyed on coiled tubing in near horizontal boreholes. The method may also be used on NMR sensors conveyed on a drilling tubular, such as a drillstring or coiled tubing for Measurement-While-Drilling (MWD) applications.

As is standard practice in well-logging, the results of the processing are recorded on a suitable medium. Implicit in the processing of the data is the use of a computer program implemented on a suitable machine-readable medium that enables the processor to perform the control and processing. The machine-readable medium may include ROMs, EPROMs, EAROMs, Flash Memories and Optical disks. These are all examples of non-transitory computer-readable media.

APPENDIX

When acoustic wave propagates through formation rocks, the wave velocity ratio $V_p/V_s$ varies with lithology of the formation and has been used as indicator of lithology based on "Pickett's crossplot". Based on the current literature, $V_p/V_s$ ratio is 1.9 for carbonate, 1.8 for dolomite, and in the range of 1.6 to 1.8 for clean sandstones. Using the grain contact theory Murphy et al. proposed in 1982, the calculated $V_p/V_s$ ratio is 1.5 for sandstone, which has also been supported by experimental data on sandstones of a wide range of porosities. Castagna et al and Han et al observed that the clay content decreases the velocities of the acoustic wave, and proposed linear empirical correlations between the wave velocity ratio and FSV.

In Biot-Gassmann theory, the acoustic wave velocity for an isotropic, non-porous media is related to the frame moduli for the formation.

The velocity of the compressional wave in a porous media can be written as:

$$\rho_c V_p^2 = K_p + K_b + \frac{4\mu}{3},$$

and the velocity of the shear wave in a porous media is $$\rho_c V_s^2 = \mu$$

where $K_p$ is defined as pore space modulus, $\mu$ is the frame shear modulus, and $K_b$ is the frame bulk modulus.

We then have the $V_p/V_s$ ratio as:

$$R^2 = \left(\frac{V_p}{V_s}\right)^2 = \frac{K_p}{N} + \frac{K_b}{N} + \frac{4}{3}$$

where $$K_p = \frac{\alpha^2}{\frac{\alpha - \phi}{K_m} + \frac{\phi}{K_f}}$$

is the pore space modulus, where $K_m$ and $K_f$ are bulk moduli for matrix materials and fluid, respectively, $\phi$ is porosity, and $\alpha$ is the Biot coefficient.

At low porosities, or in dry sand, $$\alpha = 1 - \frac{K_b}{K_m} \rightarrow 0,$$

and $K_p \rightarrow 0$. Thus $$R^2 \approx \frac{K_b}{N} + \frac{4}{3}.$$

There are many theoretical and empirical models for $K_b$ and N values. Murphy et al proposed the grain contact model, $$\frac{K_b}{\mu} = \frac{5k_n}{3[k_n + 3k_t/2]},$$

where $k_n$, $k_t$ are the normal and tangential stiffness of the grain contact. Murphy et al reported laboratory results that the $$\frac{K_b}{\mu}$$

ratio for clean sandstone (overgrowth dominated) is a constant value 0.9 independent from porosity, which form a lower bound for the ratio $V_p/V_s = \sqrt{0.9 + 4/3} = 1.5$, and stated the frame moduli $$\frac{K_b}{\mu}$$

increases non-linearly with clay content, and approaching 2.0 in shale. However, there is no literature proposed any correlation between clay content and frame moduli ratio to further link to velocity ratio. Only empirical models have been reported such as the Castagna and Han's linear correlations between $V_p/V_s$ ratio and FSV.

While the foregoing disclosure is directed to the preferred embodiments of the disclosure, various modifications will be apparent to those skilled in the art. It is intended that all variations within the scope and spirit of the appended claims be embraced by the foregoing disclosure.

What is claimed is:

1. A method of estimating a value of a porosity of an earth formation in a gas-bearing interval, the earth formation comprising the gas-bearing interval and a liquid-bearing interval, the method comprising:
    using an acoustic tool for making a measurement indicative of a porosity of the earth formation in the gas-bearing interval, the gas-bearing interval comprising:
    a first solid component having a first value of an acoustic property affecting the measurement, and
    a second solid component having a second value of an acoustic property affecting the measurement, wherein the first value is different than the second value; and
    using an at least one processor to estimate the value of the porosity in the gas-bearing interval using: (i) the measurement made by the acoustic tool, and (ii) an estimated value of the acoustic property for the gas-bearing interval determined using a fractional volume of the second solid component and a correlation between acoustic property values and corresponding fractional volumes of the second solid component in the liquid-bearing interval.

2. The method of claim 1 wherein the correlation between the acoustic property values and the corresponding fractional volumes of the second solid component in the liquid-bearing interval comprises a relationship between the acoustic property values and values of a parameter indicative of fractional volume of the second solid component, the method comprising using the at least one processor to determine the correlation by:
  estimating a corresponding value of the porosity at a plurality of depths in the liquid-bearing interval using a corresponding measurement made by a nuclear magnetic resonance (NMR) tool;
  estimating a corresponding value of the parameter at the plurality of depths in the liquid-bearing interval; and
  determining the relationship between the corresponding values of the porosity and the corresponding values of the parameter.

3. The method of claim 1 wherein the measurement is selected from the group consisting of: (i) a compressional wave slowness and (ii) a shear wave slowness.

4. The method of claim 1 wherein the first solid component further comprises quartz or carbonate and the second solid component further comprises a clay.

5. The method of claim 4 wherein the clay further comprises an authigenic clay.

6. The method of claim 2 wherein the at least one parameter further comprises at least one of: (i) a matrix slowness of a compressional velocity, (ii) a matrix slowness of a shear velocity, and (iii) a calibration factor.

7. The method of claim 2 further comprising obtaining the fractional value of the second component using at least one of: (i) a measurement made by a natural gamma ray tool, (ii) an estimate of clay bound water (CBW) using a measurement made by the NMR tool in the second interval, and (iii) an estimate of a ratio of a compressional velocity in the second interval to a shear velocity in the second interval.

8. An apparatus configured to estimate a value of a porosity of an earth formation in a gas-bearing interval, the earth formation comprising the gas-bearing interval and a liquid-bearing interval, the apparatus comprising:
  an acoustic tool configured to make a measurement indicative of a porosity of the earth formation in the gas-bearing interval, the gas-bearing interval comprising:
  a first solid component having a first value of an acoustic property affecting the measurement, and
  a second solid component having a second value of an acoustic property affecting the measurement, wherein the first value is different than the second value; and
  an at least one processor configured to:
    estimate a value of the porosity in the gas-bearing interval using the measurement made by the acoustic tool and an estimated value of the acoustic property for the gas-bearing interval determined using a fractional volume of the second solid component and a correlation between acoustic property values and corresponding fractional volumes of the second solid component in the liquid-bearing interval.

9. The apparatus of claim 8 wherein the correlation between the acoustic property values and the corresponding fractional volumes of the second solid component in the liquid-bearing interval comprises a relationship between the acoustic property values and values of a parameter indicative of fractional volume of the second solid component, and the at least one processor is configured to determine the correlation by:
  estimating a corresponding value of the porosity at a plurality of depths in the liquid-bearing interval using a corresponding measurement made by a nuclear magnetic resonance (NMR) tool;
  estimating a corresponding value of the parameter at the plurality of depths in the liquid-bearing interval; and
  determining the relationship between the corresponding values of the porosity and the corresponding values of the parameter.

10. The apparatus of claim 8 wherein the measurement is selected from: (i) a compressional wave slowness and (ii) a shear wave slowness.

11. The apparatus of claim 8 wherein the first solid component further comprises one of: (i) quartz and (ii) carbonate, and the second solid component further comprises a clay.

12. The apparatus of claim 11 wherein the clay further comprises an authigenic clay.

13. The apparatus of claim 8 wherein the at least one parameter estimated by the processor further comprises at least one of: (i) a matrix slowness of a compressional velocity, (ii) a matrix slowness of a shear velocity, and (iii) a calibration factor.

14. The apparatus of claim 8 wherein the processor is further configured to obtain the fractional value of the second component using at least one of: (i) a measurement made by a natural gamma ray tool, (ii) an estimate of clay bound water (CBW) using a measurement made by the NMR tool in the second interval, and (iii) an estimate of a ratio of a compressional velocity in the second interval to a shear velocity in the second interval.

15. The apparatus of claim 8 further comprising a conveyance device configured to convey the NMR tool into the borehole, the conveyance device selected from: (i) a wireline, and (ii) a bottomhole assembly on a drilling tubular.

16. A non-transitory computer-readable medium product having stored thereon instructions what when read by at least one processor cause the at least one processor to execute a method, the method comprising:
  estimating a value of a porosity of an earth formation in a gas-bearing interval, the earth formation comprising the gas-bearing interval and a liquid-bearing interval, using:
  a measurement made by an acoustic tool in a borehole penetrating the earth formation in the gas-bearing interval, the gas-bearing interval comprising:
    a first solid component having a first value of an acoustic property affecting the measurement, and
    a second solid component having a second value of an acoustic property affecting the measurement, wherein the first value is different than the second value; and
  an estimated value of the acoustic property for the gas-bearing interval determined using a fractional volume of the second solid component and a correlation between acoustic property values and corresponding fractional volumes of the second solid component in the liquid-bearing interval.

17. The non-transitory computer-readable medium product of claim 16 further comprising at least one of: (i) a ROMs, (ii) an EPROM, (iii) an EAROM, (iv) a flash memory, and (v) an optical disk.

18. A method of estimating a value of a porosity of an earth formation in a gas-bearing interval, the earth formation comprising the gas-bearing interval and a liquid-bearing interval, the method comprising:

using an acoustic tool for making a measurement indicative of a porosity of the earth formation in the gas-bearing interval, the gas-bearing interval comprising:
a first solid component having a first value of an acoustic property affecting the measurement, and
a second solid component having a second value of an acoustic property affecting the measurement, wherein the first value is different than the second value; and
using an at least one processor to estimate the value of the porosity in the gas-bearing interval using: (i) the measurement made by the acoustic tool, and (ii) an estimated value of a fitting parameter for an acoustic porosity model relating an additional measurement indicative of porosity made by the acoustic tool in the liquid-bearing interval to a measurement indicative of porosity by a nuclear magnetic resonance (NMR) tool in the liquid-bearing interval.

\* \* \* \* \*